(12) United States Patent
He et al.

(10) Patent No.: US 9,316,568 B2
(45) Date of Patent: Apr. 19, 2016

(54) EXPERIMENTAL METHOD FOR SIMULATING IMPACT ROCK-BURST

(75) Inventors: Manchao He, Beijing (CN); Xiaoming Sun, Beijing (CN); Xiaojie Yang, Beijing (CN)

(73) Assignee: CHINA UNIVERSITY OF MINING & TECHNOLOGY (BEIJING), Beijing (CN)

( * ) Notice: Subject to any disclaimer, the term of this patent is extended or adjusted under 35 U.S.C. 154(b) by 0 days.

(21) Appl. No.: 14/389,318

(22) PCT Filed: Mar. 31, 2012

(86) PCT No.: PCT/CN2012/073439
§ 371 (c)(1),
(2), (4) Date: Sep. 29, 2014

(87) PCT Pub. No.: WO2013/143151
PCT Pub. Date: Oct. 3, 2013

(65) Prior Publication Data
US 2015/0068319 A1    Mar. 12, 2015

(51) Int. Cl.
*G01N 3/00* (2006.01)
*G01N 3/02* (2006.01)
(Continued)

(52) U.S. Cl.
CPC ........... *G01N 3/02* (2013.01); *G01N 3/068* (2013.01); *G01N 3/30* (2013.01); *G01N 3/313* (2013.01); *G01N 24/081* (2013.01)

(58) Field of Classification Search
CPC .............. G01N 24/081; G01N 33/24; G01N 2291/0232
USPC .................. 73/760, 784, 799, 801, 838
See application file for complete search history.

(56) References Cited

U.S. PATENT DOCUMENTS

| 3,641,581 A | * | 2/1972 | Holecek | ............ G01N 3/06 346/138 |
| 4,444,058 A | | 4/1984 | Ratigan | |

(Continued)

FOREIGN PATENT DOCUMENTS

| CN | 1696646 A | 11/2005 |
| CN | 1948945 A | 4/2007 |

(Continued)

OTHER PUBLICATIONS

Wancheng Zhu et al. "Numerical Simulation on Splitting Failure Mode of Rock Under Static and Dynamic Loadings", Chinese Journal of Rock Mechanics and Engineering, Jan. 2005, Vo24.

(Continued)

*Primary Examiner* — Max Noori
(74) *Attorney, Agent, or Firm* — Yunling Ren; Eaton & Van Winkle

(57) ABSTRACT

An experimental method for simulating an impact rock-burst, comprises the following steps: making a rock sample having a through hole or a half hole; loading initial static stresses of three directions onto the rock sample; then loading dynamic load(s) by 0.5-10 minutes, to determine whether a spalling phenomenon appears on an internal surface of the hole; if appears, and the rock sample is further damaged, determining and recording a failure course, if not appears, increasing the static stress(es) or the intensity of the dynamic load, then repeating the experiment procedure as far as the rock sample goes into the failure course, then determining and recording the failure course, and ending the expierment. The impact rockburst induced by dynamic load is simulated in the rock sample successfully, and by sudying mechanical mechanisms of the rock-burst, the present application lays foundations for gradually understanding and mastering the nature of real rock burst.

20 Claims, 8 Drawing Sheets

(51) Int. Cl.
*G01N 3/313* (2006.01)
*G01N 3/06* (2006.01)
*G01N 3/30* (2006.01)
*G01N 24/08* (2006.01)

(56) References Cited

U.S. PATENT DOCUMENTS

| | | | | |
|---|---|---|---|---|
| 5,036,696 | A | * 8/1991 | Ahrens | G01N 3/307 |
| | | | | 73/12.11 |
| 6,112,599 | A | * 9/2000 | Maki, Jr. | G01N 29/11 |
| | | | | 73/587 |
| 2014/0324367 | A1 | * 10/2014 | Garvey, III | G01D 18/00 |
| | | | | 702/56 |
| 2015/0168282 | A1 | * 6/2015 | He | G01N 3/24 |
| | | | | 73/841 |

FOREIGN PATENT DOCUMENTS

| | | |
|---|---|---|
| CN | 101051011 A | 10/2007 |
| CN | 201435175 Y | 3/2010 |
| CN | 202101910 U | 1/2012 |
| CN | 102636398 A | 8/2012 |
| EP | 1001266 A1 | 5/2000 |
| EP | 1493995 A1 | 1/2005 |
| JP | 46002704 | 1/1971 |
| JP | 08005533 | 1/1996 |
| JP | 10206303 | 8/1998 |
| JP | 2002162326 | 6/2002 |
| JP | 2002195924 | 7/2002 |

OTHER PUBLICATIONS

Manchao He et al. "Experimental Study on Rockburst Processes of Granite Specimen at Great Depth", Chinese Journal of Rock Mechanics and Engineering, May 2007, vol. 26, No. 5 pp. 865.
Fuqiang Gao et al. "Numer ical Validation of RockMechan ical Properties under ImpactLoading", Blasting, Jun. 2009, vol. 26, No. 2, pp. 1-4 and pp. 14, ISSN1001-487X.
International Search Report of Application No. PCT/CN2012/073439, mailed Jan. 3, 2013.
Office Action issued Sep. 15, 2015 by the JP Office.
EESR issued Nov. 9, 2015 by the EP Office.
Numerical simulation on splitting failure mode of rock under static and dynamic loadings.
Numerical simulation on rockburst on underground opening triggered by dynamic disturbance.

* cited by examiner

EXPERIMENTAL METHOD FOR SIMULATING IMPACT ROCK-BURST

CROSS-REFERENCE TO RELATED APPLICATIONS

This is a national stage application of PCT/CN2012/073439, filed on Mar. 31, 2012 under 35 U.S.C. 371, which is incorporated reference in its entirety.

TECHNICAL FIELD

The present application generally relates to a field of deep mine engineering rock mass mechanics and geotechnical engineering research, in particular to an experimental method for simulating an impact rockburst.

BACKGROUND

Since geotechnical engineering such as mining, hydropower, railways (road) traffic tunnel, etc., are developing toward deep, a rockburst as a sort of dangerous disaster phenomenon in deep mines is happening more and more frequently. The rockburst has a nature of suddenness and violence, and when it breaks, shot rock fragments carrying with a large amount of energy threaten equipment and people, and serious one even endanger lives.

It is well known that a blasting is an indispensable construction measure for a rock excavation in recent large-scale water conservancy, tunnel, mining engineering and nuclear power engineering. When explosive blasts in a rock mass, it releases a large amount of explosive energy in a moment, generates a blasting shock wave and a stress wave which act on the surrounding rock mass in a form of a dynamic load, to make the surrounding rock mass be broken and damaged, and even generate a rock burst. However, most of recent experimental methods of laboratory simulation relating to a rockburst are implemented based on actions of static loads, and there is no experimental method implemented under actions of disturbance such as that induced by an excavation or a blasting, etc. Since a deep rock mass has specific mechanical characteristics, and research on characteristics of deep rock mass is not long at present, knowledge of rules of rockburst occurrence under the actions of disturbance is not enough. Therefore, during the excavation and the blasting, in order to study the characteristics of the rock mass under the actions of disturbance such as that induced by the excavation, the blasting, etc., inventor(s) of this application perform(s) a laboratory simulation on rockburst phenomenon based on the actions of disturbance, and provide(s) the experimental method for simulating the impact rockburst.

SUMMARY

The object of the present application is to, in part, solve the defects in prior art, and to provide an experimental method for simulating an impact rockburst.

To achieve the above object, the present application adopts technical solutions as follows:

One experimental method for simulating an impact rockburst may include:

S1: making a rock sample specimen having a through hole or a half hole;

S2: loading initial static stresses of three directions onto the rock sample specimen, and maintaining the initial static stresses of the three directions, to simulate a situation that an excavated tunnel suffers the static stresses;

S3: loading dynamic load(s) of one direction, two directions or three directions onto the rock sample specimen by 0.5-10 minutes, so as to determine whether a spalling phenomenon appears on an internal surface of the through hole or the half hole, wherein the dynamic load(s) is used to simulate the disturbance induced by an excavation, a blasting, an earthquake or a mechanical vibration;

S4: under an action of the dynamic load(s) in the step S3, if it is determined that the spalling phenomenon appears on the internal surface of the hole, unceasingly maintaining a state of loading the dynamic load(s) in the step S3 by 0.5-10 minutes, to determine whether the rock sample specimen is further damaged, and if the rock sample specimen is not further damaged, stopping the loading the dynamic load, and increasing the static stress(es) of one direction, two directions or three directions loaded onto the rock sample specimen, then repeating the step S2 and the following experimental steps, and if the rock sample specimen goes into a failure course, determining and recording the failure course, and ending the experiment of the impact rockburst; and S5: under the action of the dynaimc load in the step S3, if it is determined that no spalling phenomenon appears on the internal surface of the hole, unceasingly maintaining the state of loading the dynaim load in the step S3 by 2-10 minutes, to determine whether the spalling phenomenon appears in the rock sample specimen, and if it is determined that the spalling phenomenon appears on the internal surface of the hole of the rock sample specimen, repeating the step S4 and the following experimental steps, and if it is determined that no spalling phenomenon appears on the internal surface of the hole of the rock sample specimen, stopping the loading the dynamic load, and increasing the static stress(es) of the one direction, the two directions or the three directions loaded onto the rock sample specimen, then repeating the step S2 and the following experimental steps, and if the rock sample specimen goes into the failure course, determining and recording the failure course, and ending the experiment of the impact rockburst.

Another experimental method for simulating an impact rockburst of the present application may include:

S1: making a rock sample specimen having a through hole or a half hole;

S2: loading initial static stresses of three directions onto the rock sample specimen, and maintaining the initial static stresses of the three directions, to simulate a situation that an excavated tunnel suffers the static stresses;

S3: loading dynamic load(s) of one direction, two directions or three directions onto the rock sample specimen by 0.5-10 minutes, so as to determine whether a spalling phenomenon appears on an internal surface of the through hole or the half hole, wherein the dynamic load is used to simulate the disturbance wave induced by an excavation, a blasting, an earthquake or a mechanical vibration;

S4: under an action of the dynamic load in the step S3, if it is determined that the spalling phenomenon appears on the internal surface of the hole, unceasingly maintaining a state of loading the dynamic load in the step S3 by 0.5-10 minutes, to determine whether the rock sample specimen is further damaged, and if the rock sample specimen is not further damaged, stopping the loading the dynamic load, and increasing an intensity value of the dynamic load, then repeating the step S3 and the following experimental steps, and if the rock sample specimen goes into a failure course, determining and recording the failure course, and ending the experiment of the impact rockburst; and S5: under the action of the dynamic load in the step S3, if it is determined that no spalling phenomenon appears on the internal surface of the hole, unceasingly maintaining the state of loading the dynamic load in the step S3 by 2-10 minutes, to determine whether the spalling phenomenon appears in the rock sample specimen, and if it is determined that the spalling phenomenon appears on the internal surface of the hole of the rock sample specimen, repeating the step S4 and the following experimental steps, and if it is determined that no spalling phenomenon appears on the internal surface of the hole of the rock sample specimen, stopping the loading the dynamic load, and increasing the intensity value of the dynamic load, then repeating the step S3 and the following experimental steps, and if the rock sample specimen goes into the failure course, determining and recording the failure course, and ending the experiment of the impact rockburst.

Furthermore, in the above experimental methods for simulating an impact rockburst:

In the step S1, the rock sample specimen is obtained from a rock mass at a site to be excavated.

In the step S4 and S5, if the rock sample specimen is not damaged, after the loading the dynamic load(s) is stopped, increasing the static stress(es) of the one direction, the two directions or the three directions loaded onto the rock sample specimen, wherein an increased amount of the static stress(es) of the one direction, the two directions or the three directions is(are) of the same intensity as that of the dynamic load(s) loaded onto the rock sample specimen in the step S3.

In the step S2, the manner of loading the static stresses is a force loading manner or a strain loading manner, wherein, when the strain loading method is adopted, a loading rate is 0.004-0.2 mm/s, and when the force loading method is adopted, the loading rate is 0.05-2 kN/s.

In the step S1, a cross section of the through hole or the half hole in the rock sample specimen has a shape of circular, half circular, or horseshoe.

In the step S1, the rock sample specimen is made in a joint structure, and the rock sample specimen made in the joint structure is obtained by being collected from the site and then being further processed, or made by the following steps: (1) making up a plurality of plasterboards or resin plates, and drying the plurality of the plasterboards or the resin plates by air, wherein each of the plasterboards has a thickness of 5~10 mm, and each of the resin plates has a thickness of 3~8 mm; (2) bonding the plurality of the dried plasterboards or the dried resin plates together to form a laminate body by using an adhesive, and then drying the laminate body by air; (3) cutting the dried laminate body of the plasterboards into a required size according to a joint strike, and forming the hole at a position of a centre line of the laminate body, so as to obtain the rock sample specimen in the joint structure.

In the step S3, a disturbance signal of the dynamic load comprises: a cyclic wave disturbance signal, a single pulse disturbance signal, a step pulse disturbance signal, a noise wave disturbance signal, or a complex wave disturbance signal formed by superposing any of the above cyclic wave disturbance signal with a slope wave, or a superposed disturbance signal formed by superposing the complex wave disturbance signal with the noise wave disturbance signal.

Wherein the method further comprises a step of recording and/or a step of photographing, wherein, when the phenomenon appears on the surface of the rock sample specimen, the failure course is recorded and/or photographed by using a micro camera.

In accordance with the above technical solution, it may be seen that, advantages and positive effects of the experimental method for simulating an impact rockburst of the present application lie in: in the experimental method for simulating an impact rockburst of the present application, the rock sample specimen has the hole, which veritably simulates a real situation of a site or a tunnel to be excavated or blasted etc. In the present application, by loading dynamic load(s) of the one direction, the two directions or the three directions and the dynamic load onto the rock sample specimen, the situation of a site or a tunnel to be excavated or blasted etc., suffers the static stresses and the dynamic load may be simulated veritably. According to designs of experiments, different static stress loads and dynamic loads may be loaded on the rock sample specimen according to different geological depths. Furthermore, different types of dynamic loads may be designed according to real situations in the sites to be excavated, which may be for example a pulse wave or a noise wave, etc., so as to veritably simulate the dynamic loads generated by mechanical vibrations, an earthquake or man-made excavating actions. The present application may successfully conduct the rockburst phenomenon to occur in the rock sample specimen through the actions of the dynamic load. By studying mechanisms of the rock burst phenomenon on the rock sample specimen, the present application lays foundations for gradually understanding and mastering the nature of real rockburst phenomenon. Particularly, when the rock sample specimen is obtained from the sites to be excavated or to be blasted, by simulating a disaster phenomenon of the rockburst on the rock sample specimen, and fully analyzing the course and phenomenon of the rockburst, it may be helpful for accurately finding weak portions which are sensitive to the actions of excavation or blasting impact, such that strengthening support measures may be adopted with regard to the weak portions, so as to achieve the object of maintaining construction safety, and ensure mining workings, etc., to be progressed smoothly.

By the following illustrations on the preferred embodiments of the present application with reference to accompanying drawings, the above and other objects, features and advantages of the present application will become more distinct.

DESCRIPTION OF THE EMBODIMENTS

The embodiments of the present application will be illustrated in detail as follows. Here the described embodiments are used to illustrate the present application, but not used to limit the present application.

In the experimental method for simulating an impact rockburst according to the embodiments of the present application, a direction of axis X, a direction of axis Y, and a direction of axis Z are perpendicular to one another to construct a three-dimension space. The direction of axis X and the direction of axis Z are in horizontal directions. The direction of axis Y is in a vertical direction.

Embodiment 1

Figure 1:
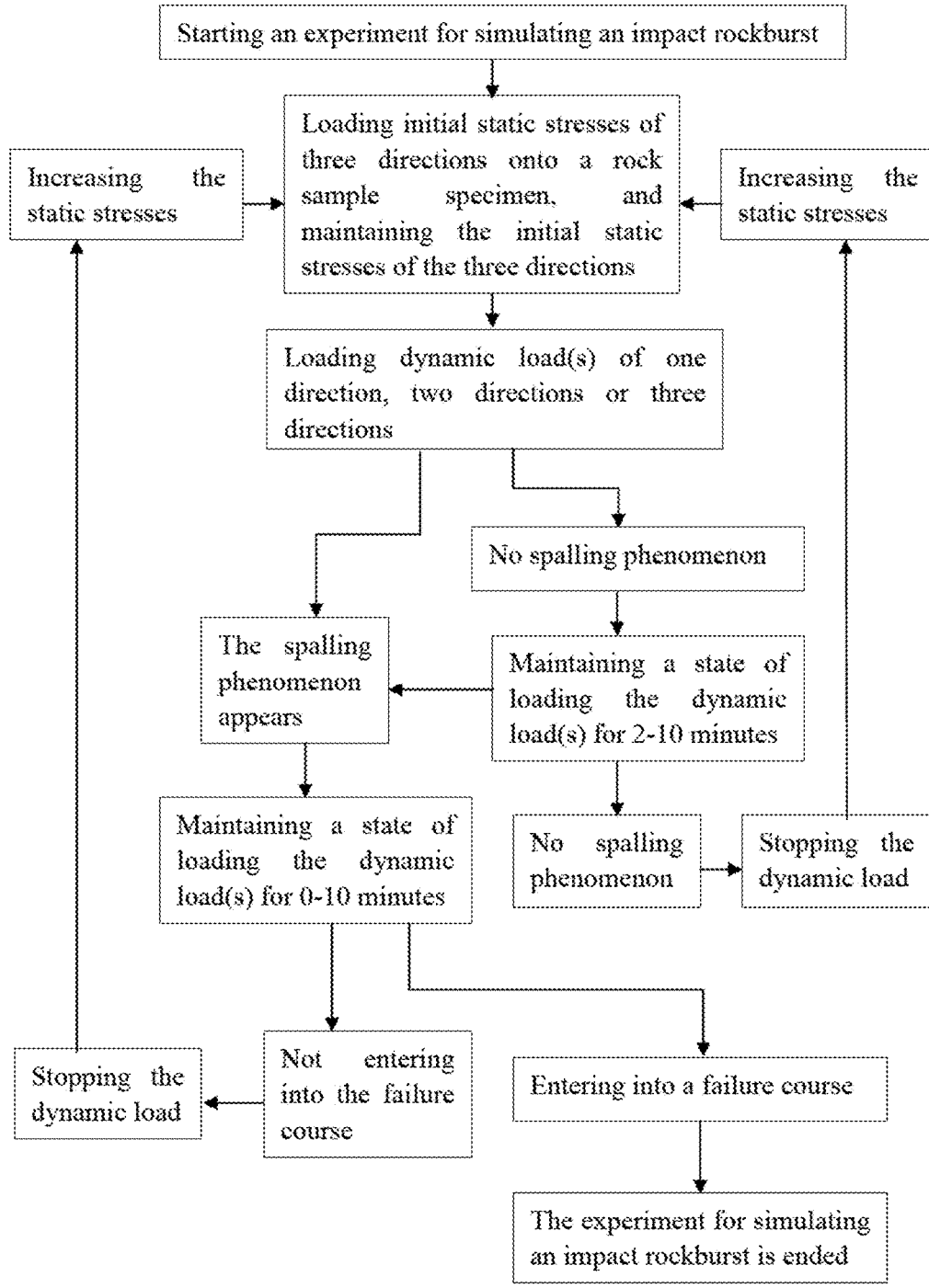
FIG. 1 is a flowchart of an experimental method for simulating an impact rockburst according to a first embodiment of the present application.
Figure 2A:
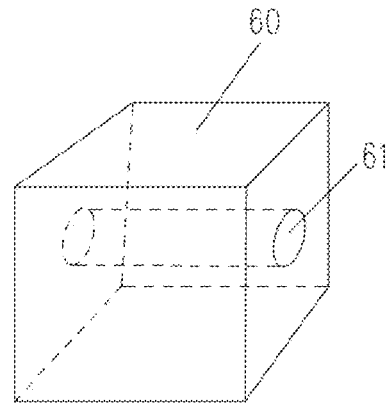
FIGS. 2A to 2E are structure diagrams of specimens used in the experimental method for simulating an impact rockburst according to an embodiment of the present application.
Figure 2C:
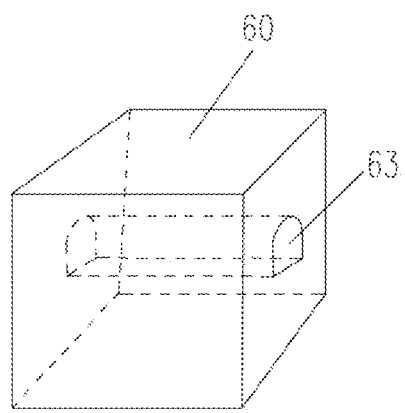
Figure 2B:
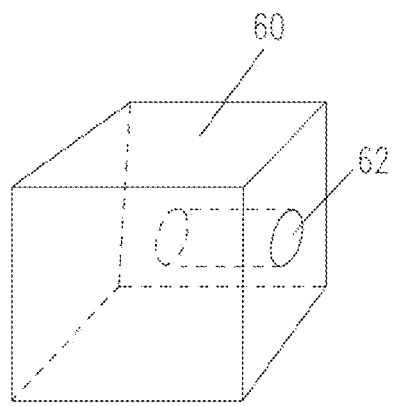
Figure 2D:
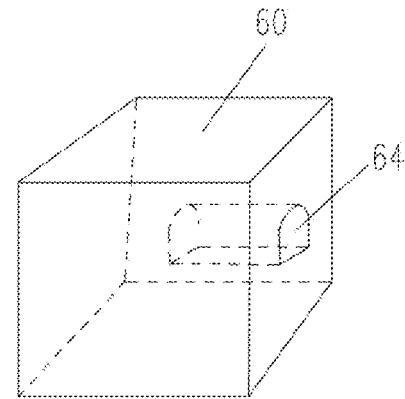

As shown in FIG. 1, the experimental method for simulating an impact rockburst according to the first embodiment of the present application may include the steps as follows:

S1: a rock sample specimen 60 is made. A centre of the rock sample specimen 60 has a through hole 61 having a circular cross section (as shown in FIG. 2A), a half hole 62 having a circular cross section (as shown in FIG. 2B), a through hole 63 having a horseshoe cross section (as shown in FIG. 2C) or a half hole 64 having a horseshoe cross section (as shown in FIG. 2D). The holes of the rock sample specimen 60 are generally through holes and half holes, but cross section shapes of the holes may be various, not be limited to circular or horseshoe. The rock sample specimens may be made in a laboratory, or may be obtained from a rock mass at a site to be excavated. Adopting the rock mass at the site to be excavated may not only facilitate studying a mechanical mechanism of the rockburst, but also facilitate guiding the real excavation and blasting at the site.

S2: initial static stresses of three directions are loaded onto the rock sample specimen, and maintained, to simulate a situation that an excavated tunnel suffers the static stresses. Wherein a manner of loading the static stresses is a force loading manner or a strain loading manner. Wherein when the strain loading method is adopted, a loading rate is 0.004-0.2 mm/s, and when the force loading method is adopted, the loading rate is 0.05-2 kN/s.

S3: dynamic load(s) of one direction, two directions or three directions is(are) loaded onto the rock sample specimen by 0.5-10 minutes, so as to determine whether a spalling phenomenon appears on an internal surface of the through hole or the half hole. Wherein the dynamic load is used to simulate the disturbance wave induced by an excavation, a blasting, an earthquake or a mechanical vibration.

S4: under an action of the dynamic load in the step S3, if it is determined that the spalling phenomenon appears on the internal surface of the hole, a state of loading the dynamic load in the step S3 is unceasingly maintained by 0.5-10 minutes, to determine whether the rock sample specimen is further damaged. If the rock sample specimen is not further damaged, the loading the dynamic load is stopped, and the static stress(es) of one direction, two directions or three directions loaded onto the rock sample specimen is(are) increased. An increased amount of the static stress(es) of the one direction, the two directions or the three directions may be of the same intensity as that of the dynamic load loaded onto the rock sample specimen in the step S3, and it may not be limited thereto, and may be other amounts. After the static stresses of the three directions loaded onto the rock sample specimen are increased, the step S2 and the following experimental steps are repeated. If the rock sample specimen goes into a failure course, the failure course is determined and recorded, and an experiment of the impact rockburst is ended. In another case, under the action of the dynamic load in the step S3, the spalling phenomenon appears on the internal surface of the hole, then further damage phenomenon appears immediately and develops into the rockburst, and then the failure course is determined and recorded directly, and the experiment of the impact rockburst is ended.

S5: under the action of the dynamic load in the step S3, if it is determined that no spalling phenomenon appears on the internal surface of the hole, the state of loading the dynamic load in the step S3 is unceasingly maintained by 2-10 minutes, to determine whether the spalling phenomenon appears in the rock sample specimen. If the spalling phenomenon appears on the internal surface of the hole of the rock sample specimen, the step S4 and the following experimental steps are repeated. If no spalling phenomenon appears on the internal surface of the hole of the rock sample specimen, the loading the dynamic load is stopped, and the static stress(es) of the one direction, the two directions or the three directions loaded onto the rock sample specimen is(are) increased. The increased amount of the static stress(es) of the one direction, the two directions or the three directions may be of the same intensity as that of the dynamic load loaded onto the rock sample specimen in the step S3, and it may not be limited thereto, and may be other amounts. After the static stresses of the three directions loaded onto the rock sample specimen are increased, the step S2 and the following experimental steps are repeated. If the rock sample specimen goes into the failure course, an experimental route diagram, an amplitude and frequency, an occurred phenomenon and moment, a stress, strain, etc., of a course of the impact rockburst are determined and recorded, and the experiment of the impact rockburst is ended.

In the above described experiment procedure, the method further includes a step of recording or photographing the failure course by using a micro camera. That is, when the spalling phenomenon on the surface of the rock sample specimen is determined, and/or when the rock sample specimen goes into the failure course, the failure course is recorded or photographed, or both recorded and photographed, by using the micro camera.

Figure 2E:
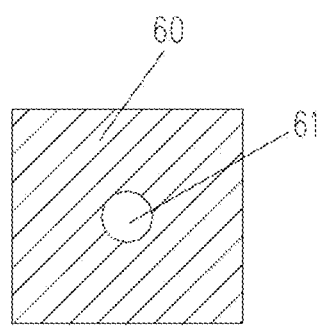
Figure 3:
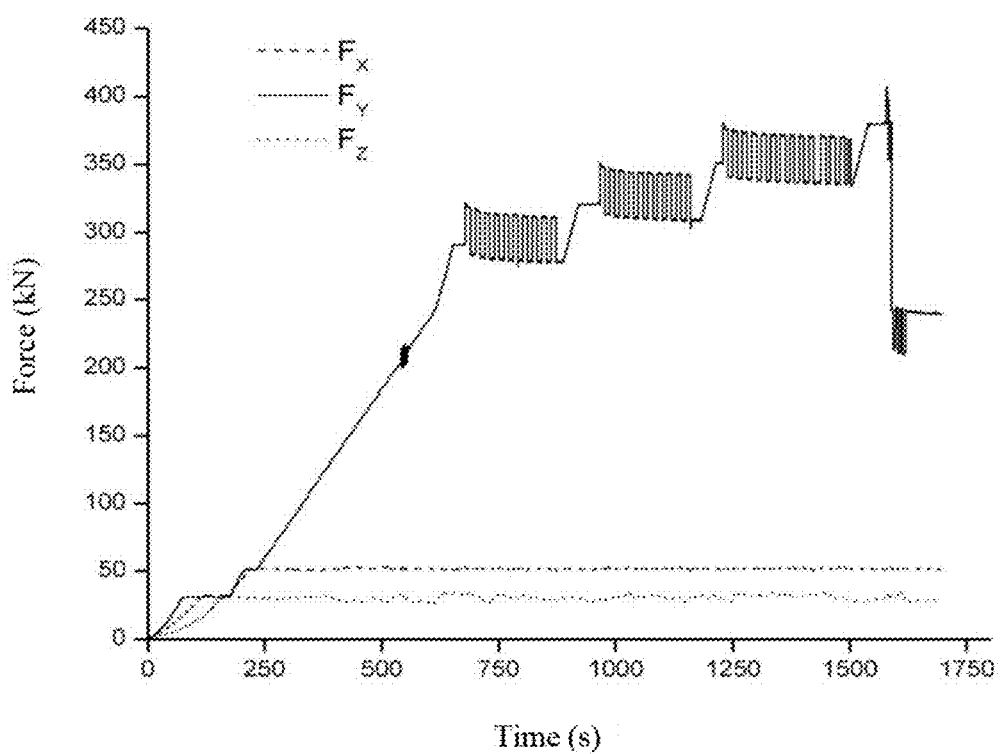
FIG. 3 is an experimental route diagram of the experimental method for simulating an impact rockburst according to a first experimental example of the present application.

As shown in FIG. 2E, in the step S1 of the above experiment, the rock sample specimen may be made in a joint structure. Concretely, the rock sample specimen may be made by the following steps: (1) by simulating the rock mass at the site, a plurality of plasterboards or resin plates are made up, and then dried by air, wherein each of the plasterboards has a thickness of 5~10 mm, and each of the resin plates has a thickness of 3~8 mm. (2) the plurality of the dried plasterboards or the dried resin plates are bonded together to form a laminate body by using an adhesive, and then the laminate body is dried by air. (3) by simulating a joint strike of the rock mass at the site, the dried laminate body of the plasterboards is cut into a required size, for example, a cube of 160×160× 160 mm, and the hole is formed at a position of a centre line of the laminate body, such that the rock sample specimen in the joint structure is obtained. Such rock sample specimen in the joint structure may also be obtained by being collected from the site to be excavated or blasted and then being further processed.

As shown in Table 1, in the step S3 of the above experiment, a signal of the dynamic load loaded onto the rock sample specimen may be: a cyclic wave disturbance signal, a single pulse disturbance signal (used to simulate a rock burst or a blasting shock), a step pulse disturbance signal, a noise wave disturbance signal (used to simulate vibrations of construction machinery, vibrations of mining car running, and a disturbance signal of an earthquake wave), or a complex wave disturbance signal formed by superposing any of the above cyclic wave disturbance signal with a slope wave, or a superposed disturbance signal formed by superposing the complex wave disturbance signal with the noise wave disturbance signal. Wherein the single pulse disturbance signal includes sine wave, triangle wave, regular sawtooth wave, square wave, etc., and both the pulse width and the pulse amplitude of the single pulse disturbance signal may be adjusted. The step pulse disturbance signal includes semi sine wave, semi triangle wave, semi regular sawtooth wave, semi square wave, etc., and both the pulse width and the pulse amplitude of the step pulse disturbance signal may be adjusted. Some types of typical disturbance signals are illustrated as shown in the Table 1.

TABLE 1

| No. | Waveform name | Waveform sketch |
|---|---|---|
| 1 | Sine wave | 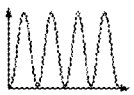 |
| 2 | Triangle wave | 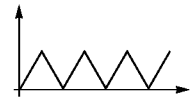 |
| 3 | Regular sawtooth wave | 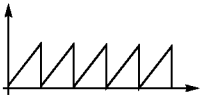 |
| 4 | Square wave | 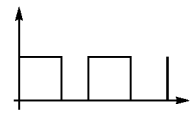 |
| 5 | Uniform white noise |  |
| 6 | Gaussian white noise |  |
| 7 | Periodic random white noise |  |
| 8 | Complex wave formed by superposing a slope wave with a cyclic wave |  |

TABLE 1-continued

| No. | Waveform name | Waveform sketch |
|---|---|---|
| 9 | Complex wave formed by superposing a slope wave with a noise wave |  |
| 10 | Complex wave formed by superposing a cyclic wave with a noise wave |  |
| 11 | Complex wave formed by superposing a slope wave with a cyclic wave and a noise wave |  |
| 12 | Loading a single pulse | 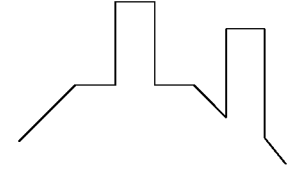 |
| 13 | Unloading a single pulse | 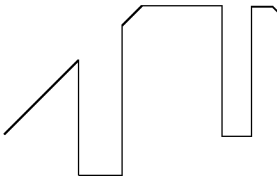 |
| 14 | Loading a step pulse | 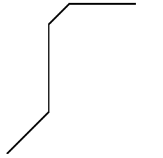 |
| 15 | Unloading a step pulse | 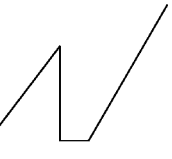 |

EXPERIMENTAL EXAMPLE 1

Referring to FIGS. 3 and 4A to 4F, when the experimental method for simulating an impact rockburst according to the above first embodiment is used, the rock sample specimen therein is a sandstone rock mass obtained from the site to be excavated, which is a cube of 110×110×110 having a circular through hole with a diameter of 50 mm, and an uniaxial strength of the rock sample specimen is 68 MPa. In the step S2, the initial static stresses of three directions loaded onto the rock sample specimen are respectively: a static stress FX of direction X: 30 kN, a static stress FY of direction Y: 290 kN, and a static stress FZ of direction Z: 50 kN, wherein the loading rate is 0.5 kN/s when the force loading manner is adopted. The type of the dynamic load in the step S3 is a square wave (with an amplitude of 0.1 mm and a frequency of 0.05 Hz), which disturbs only in the direction Y and is applied by 3 minutes, and no spalling phenomenon appears on the internal surface of the through hole of the rock sample specimen, the dynamic load is stopped. Then the static stress of the direction Y is increased to 320 kN, and the same dynamic load is applied by 3 minutes for determination, and still no spalling phenomenon appears on the internal surface of the through hole of the rock sample specimen, the dynamic load is stopped. Then the static stress of the direction Y is further increased to 350 kN, and the same dynamic load is applied, and it is determined that a spalling phenomenon and cracking phenomenon along with sounds at the same time appears on the internal surface of the through hole of the rock sample specimen, then the state of loading the load by 3 minutes, and the cracking does not extend and no further damage is produced, the dynamic load is stopped. Then the static stress is further increased to 380 kN, and the same dynamic load is applied, then a severe rockburst phenomenon occurs in the rock sample specimen, a large amount of rock fragments shoot out along with loud noises, and then the experiment is ended.

Figure 4A:
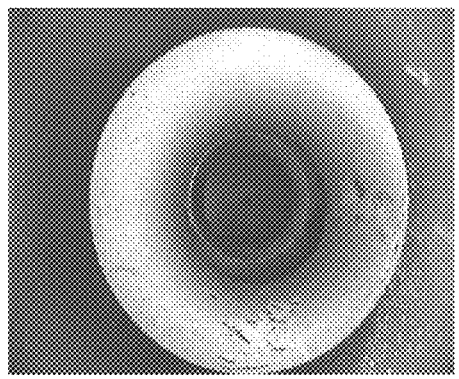
FIGS. 4A to 4F are photographs of a rockburst course taken during an experiment procedure in the experimental method for simulating an impact rockburst according to the first experimental example of the present disclosure.
Figure 4B:
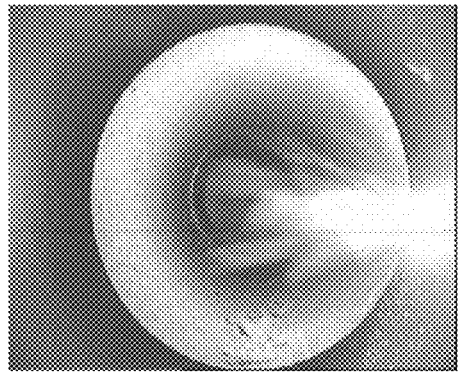
Figure 4C:
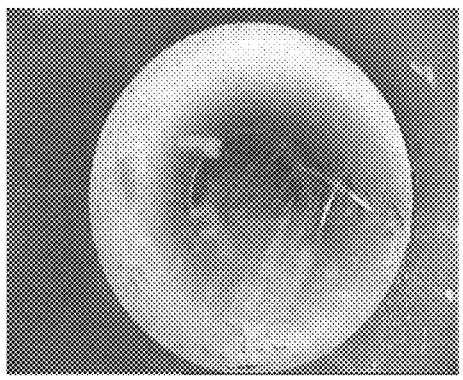
Figure 4D:
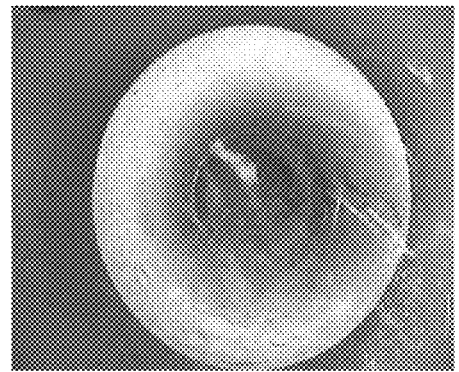
Figure 4E:
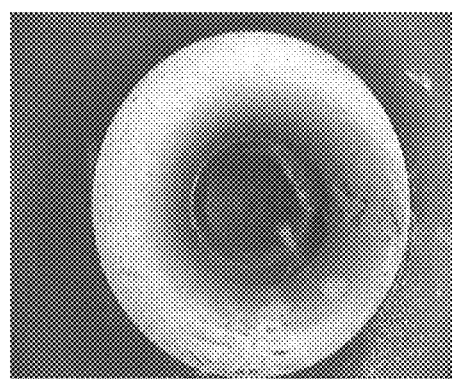
Figure 4F:
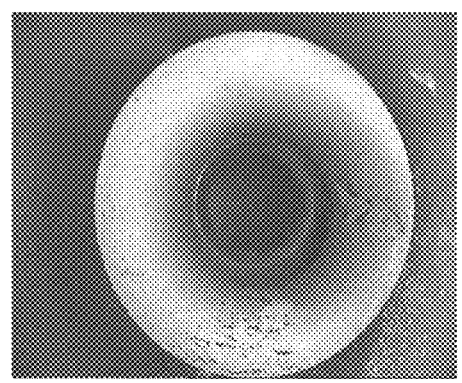

FIGS. 4A to 4F are photographs taken by a micro camera during the above experiment procedure. FIG. 4A shows that the spalling phenomenon appears on the internal surface of the through hole of the rock sample specimen, along with crack extension. FIG. 4B shows that the rockburst occurs, and a lot of rock fragments shoot out along with noises. FIG. 4C shows that the rockburst phenomenon is fading along with the rock fragments shooting out. FIG. 4D shows that a few rock fragments shoot out along with diminishing sounds. FIG. 4E shows that the rock fragments shoot slightly and the sound almost disappears. FIG. 4F shows that the rockburst is ended, apparent cracks are produced, and the sound disappears.

Figure 5:
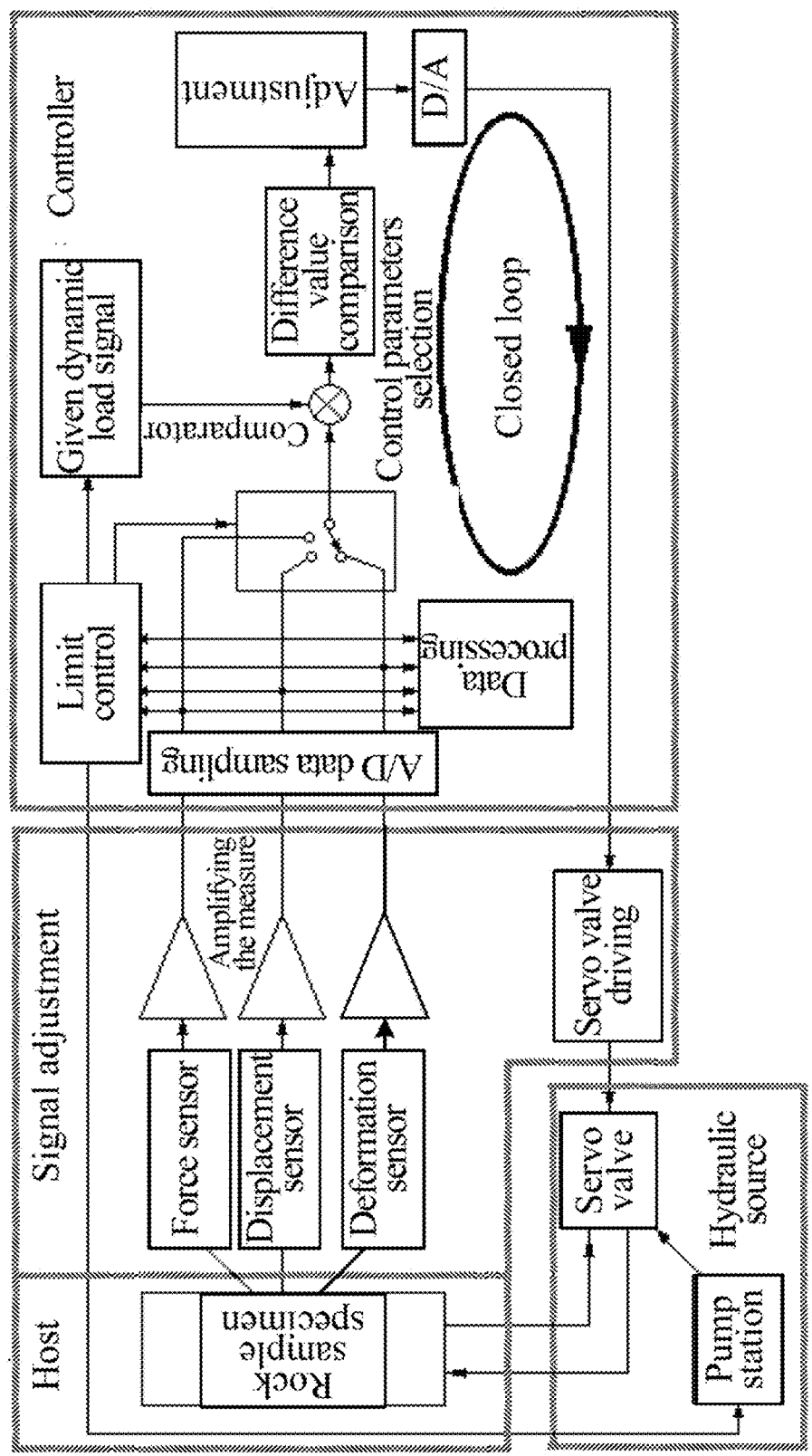
FIG. 5 is a block diagram of loading a disturbance signal onto a rock sample specimen in the experimental method for simulating an impact rockburst according to the first experimental example of the present application.

As shown in FIG. 5, in the present application, the disturbance signal of dynamic load may be loaded on the rock sample specimen through a control system. Wherein the control system includes three control systems not only being independent respectively but also being coordinated to one another, which are configured to load the dynamic load on the rock sample specimen in the direction of axis X, the direction of axis Y, and the direction of axis Z respectively. Wherein each control system has control parameters of force and actuator displacement, etc., and when one of the control parameters is selected, a control loop of the selected parameter may be set up, and unselected parameters (desired test results) are functions of the selected parameter (test condition). The control systems are fully digitalized and controlled by controllers or a controller, and each of the control systems has the same constitution and working principle. As shown in FIG. 5, the control system includes: a plurality of sensors, a hydraulic source and a controller. Wherein the plurality of sensors are configured to obtain forces, displacements or deformations suffered by the rock sample specimen. The hydraulic source includes a pump station and a servo valve, the pump station is configured to supply hydraulic oil to a loading hydraulic cylinder of direction X and/or a loading hydraulic cylinder of direction Y and/or a loading hydraulic cylinder of direction Z, and the servo valve includes at least a regulating valve and at least a reversing valve. The controller is configured to receive signals obtained from the plurality of sensors, and compares the signals with a value of an input given dynamic load signal, to obtain difference values. The controller performs a correction adjustment according to the difference values, to control opening(s) of the regulating valve(s), so as to control respective oil inlet amount or oil return amount, and oil inlet rate or oil return rate of the loading hydraulic cylinder of direction X and/or the loading hydraulic cylinder of direction Y and/or the loading hydraulic cylinder of direction Z, so as to further control displacements moved or forces suffered by respective piston rods of the loading hydraulic cylinder of direction X and/or the loading hydraulic cylinder of direction Y and/or the loading hydraulic cylinder of direction Z. Meanwhile, the controller controls the reversing valve to be reversed. Finally, the sizes of the displacements moved or the forces suffered by the respective piston rods of the loading hydraulic cylinder of direction X and/or the loading hydraulic cylinder of direction Y and/or the loading hydraulic cylinder of direction Z are consistent with the forces, the displacements or the deformations expressed by the input dynamic load signal. The control system in the present application further has a function for alarming. When values measured by the sensors are over a set range of limit control values, the control system alarms, controls the servo valve to be shut off, to cut off oil paths and withdraw oil pressure, so as to protect the rock sample specimen from accidental damage. Meanwhile, the pump station stops working. Also, when the values of the given dynamic load signal are over a set range of limit control values, the control system alarms. Moreover, the control system in the application may perform data processing with respect to data measured by the sensors: to extract signal values measured by the sensors and to deduce valuable and meaningful data, for example, to generate a force-time curve, a displacement-time curve, a stress-strain relationship curve, etc.

In the present application, the hydraulic source outputs a large amount of high pressure oil into the servo valve. The control parameters (test forces, specimen deformations or piston strokes) and the given dynamic load signals can be selected by an operator according to an experimental purpose. The given dynamic load signal is input to a comparator and compared with the values measured by the sensors, so as to obtain the difference values, and to drive the servo valve after an adjustment according to the difference values. Through the servo valve (which can adopts a structure in the prior art), electrical quantities may be transferred into oil flows to drive the hydraulic cylinder piston to apply forces onto the rock sample specimen. Through the sensors, non-electrical physical quantities (forces, deformations and displacements) are transferred into electrical signals. After the electrical signals are amplified, they are compared with the given signals in the comparator. Output difference values are used by the regulator to adjust correction deviations, so as to make the non-electrical physical quantities for controlling the rock sample specimen quickly and accurately follow the given signals with certain accuracy.

However, the manner of loading the dynamic load may use any other manners in the prior art, and in fact, it is basically the same as the manner of loading the static load. Merely, in the manner of loading the static load, stress values are changed linearly, while in the manner of loading the dynamic load, the stress values are changed in consistent with changes of a selected dynamic load signal.

Embodiment 2

Figure 6:
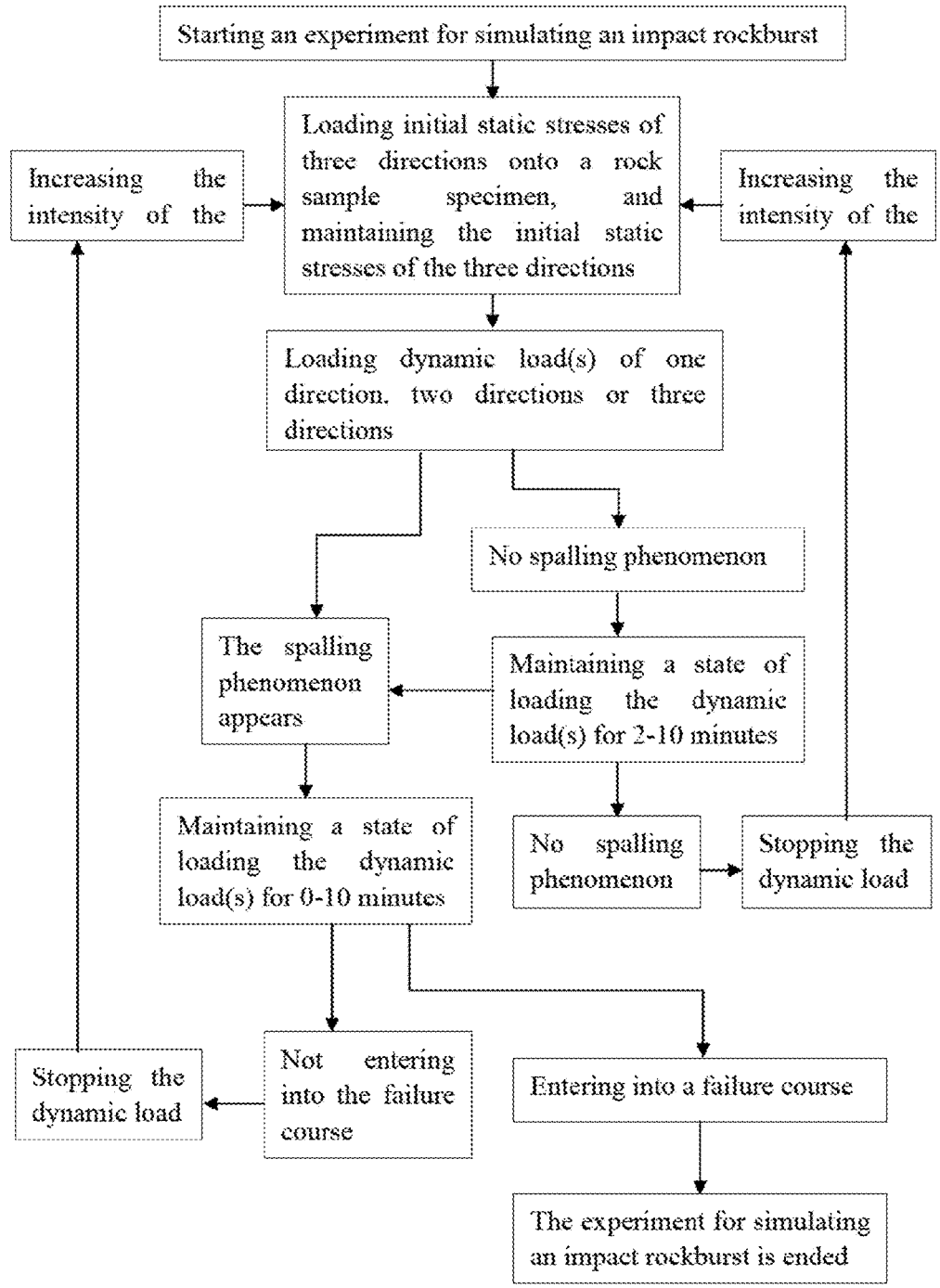
FIG. 6 is a flowchart of the experimental method for simulating an impact rockburst according to a second embodiment of the present application.

As shown in FIG. 6, steps of an experimental method for simulating an impact rockburst according to a second embodiment of the present application are basically the same as that of the first embodiment, and differences only lie in: in the step S4 and S5 of the first embodiment, when no rockburst occurs in the rock sample specimen, after the static stresses value of the three directions loaded onto the rock sample specimen are increased, the rest experiment steps are repeated (that is to repeat the step S2 and the following experiment steps); however, in step S4 and S5 of the second embodiment, when no rockburst occurs in the rock sample specimen, after a dynamic load loaded onto the rock sample specimen are increased, rest experiment steps are repeated (that is to repeat step S3 and following experiment steps), and finally, a rockburst phenomenon is conducted to occurs successfully. Rest steps of the second embodiment, which are the same as the first embodiment, are not repeated here any more.

EXPERIMENTAL EXAMPLE 2

Figure 7:
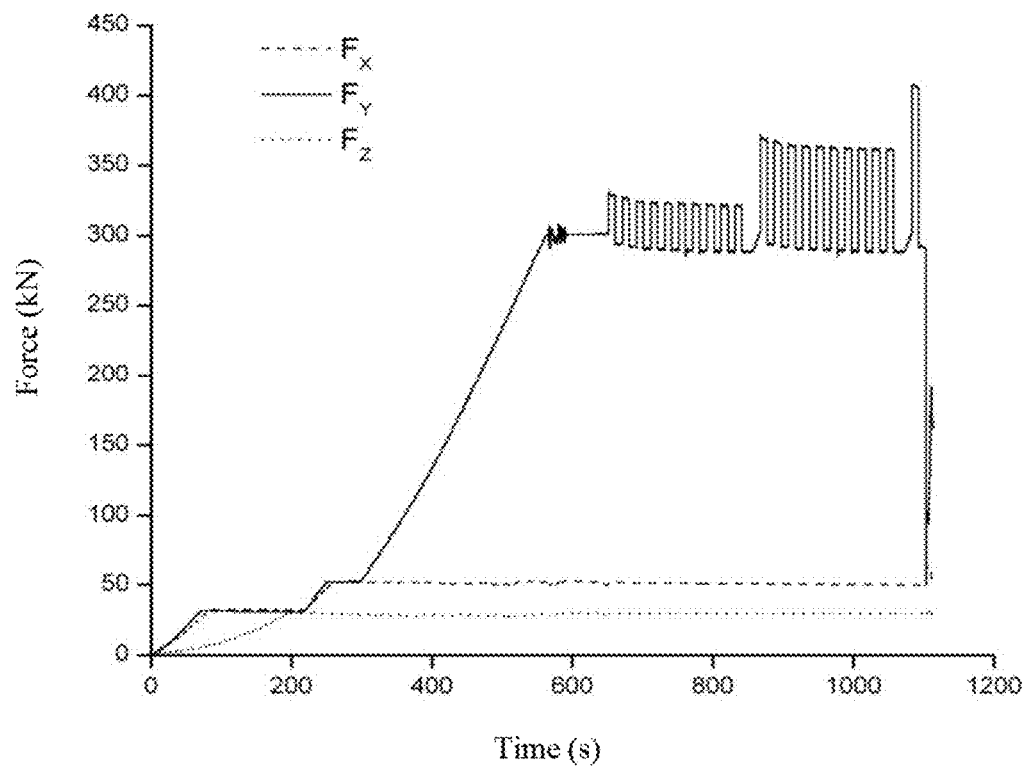
FIG. 7 is an experimental route diagram of the experimental method for simulating an impact rockburst according to the second experimental example of the present application.

Referring to FIG. 7, the experimental method for simulating an impact-type rock burst according to the second embodiment is used, wherein the rock sample specimen is a sandstone rock mass obtained from the site to be excavated, which is a cube of 110×110×110 mm having a circular through hole with a diameter of 50 mm, and an uniaxial strength of the rock sample specimen is 73 MPa. In step S2, initial static stresses of three directions loaded onto the rock sample specimen are respectively: a static stress FX of direction X: 30 kN, a static stress FY of direction Y: 350 kN, and a static stress FZ of direction Z: 50 kN, wherein a loading rate is 0.5 kN/s when a force loading manner is adopted. A type of a dynamic load in the step S3 is a square wave (with an amplitude of 0.1 mm and a frequency of 0.05 Hz), which perturbs only in the direction Y and is applied by 3 minutes, and no spalling phenomenon appears on an internal surface of the through hole of the rock sample specimen, the dynamic load is stopped. Then the disturbance intensity of the dynamic load of the direction Y is increased, that is, the amplitude of the dynamic load of the direction Y is increased to 0.2 mm, and the frequency is still 0.05 Hz, then it is determined immediately that a spalling phenomenon and cracking phenomenon along with sounds at the same time appears on the internal surface of the through hole of the rock sample specimen, then a state of loading the load by 3 minutes, the cracking does not extend and no further damage is produced on the internal surface of the through hole of the rock sample specimen, then the dynamic load is stopped. Then the amplitude of the dynamic load is increased to 0.3 mm, and the frequency is still 0.05 Hz, then a severe rockburst phenomenon occurs in the rock sample specimen, a lot of rock fragments shoot out along with loud noises, and then the experiment is ended.

Figure 8A:
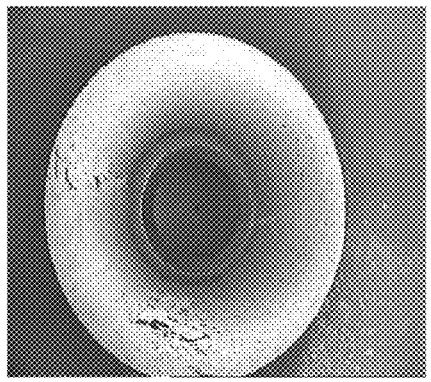
FIGS. 8A to 8F are photographs of a rockburst course taken during an experiment procedure in the experimental method for simulating an impact rockburst according to the second experimental example of the present disclosure.
Figure 8B:
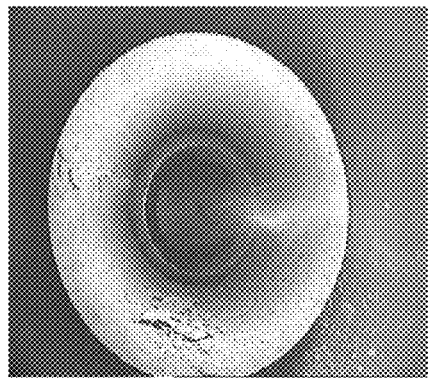
Figure 8C:
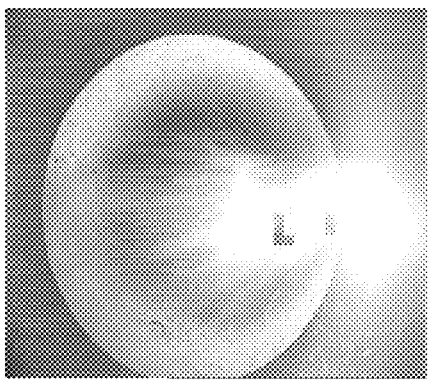
Figure 8D:
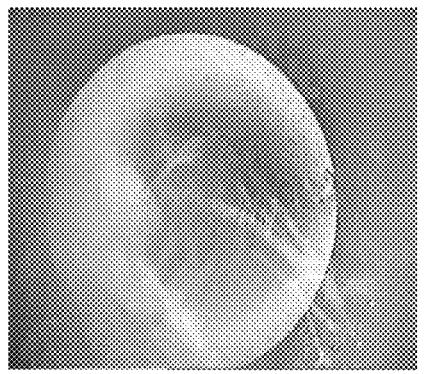
Figure 8E:
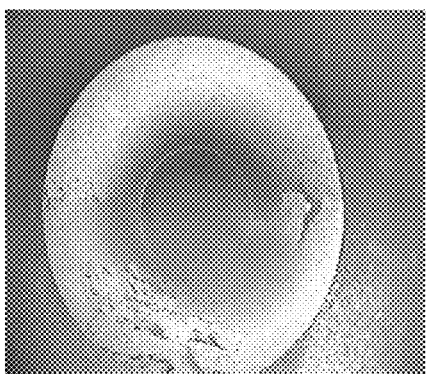
Figure 8F:

FIGS. 8A to 8F are photographs taken by a micro camera during the above experiment procedure. FIG. 8A shows that the spalling phenomenon appears on the internal surface of the through hole of the rock sample specimen, along with crack extension. FIG. 8B shows that the rockburst occurs, and the rock fragments shoot out along with loud noises. FIG. 8C shows that the rockburst phenomenon increases along with a lot of rock fragments shooting out, and the noises increase. FIG. 8D shows that the rockburst phenomenon is fading along with the rock fragments shooting out and diminishing sounds. FIG. 8E shows that the rock burst is ended, and the rock sample specimen is broken and collapsed. FIG. 8F shows that the rock sample specimen is completely collapsed and failure.

Although the present application has been illustrated by referring to several typical embodiments, it should be understood that terms used in the present application are only for illustrative and exemplary purposes, rather than restrictive terms. Since the present application may be implemented concretely in various forms without departing from spirit and substance of the present application, it should be understood that the above embodiments are not limited to any details described above, but should be explained broadly within the spirit and scope defined in appended claims. Therefore, all changes and modifications falling into the claims and their equivalent scope should be looked as being covered by the claims.

What is claimed is:

1. An experimental method for simulating an impact rockburst, the method comprising:
    S1: making a rock sample specimen having a through hole or a half hole;
    S2: loading initial static stresses of three directions onto the rock sample specimen, and maintaining the initial static stresses of the three directions, to simulate a situation that an excavated tunnel suffers the static stresses;
    S3: loading dynamic load(s) of one direction, two directions or three directions onto the rock sample specimen by 0.5-10 minutes, so as to determine whether a spalling phenomenon appears on an internal surface of the through hole or the half hole, wherein the dynamic load is used to simulate the disturbance wave induced by an excavation, a blasting, an earthquake or a mechanical vibration;
    S4: under an action of the dynamic load in the step S3, if it is determined that the spalling phenomenon appears on the internal surface of the hole, unceasingly maintaining a state of loading the dynamic load in the step S3 by 0.5-10 minutes, to determine whether the rock sample specimen is further damaged, and if the rock sample specimen is not further damaged, stopping the loading the dynamic load, and increasing the static stress(es) of one direction, two directions or three directions loaded onto the rock sample specimen, then repeating the step S2 and the following experimental steps, and if the rock sample specimen goes into a failure course, determining and recording the failure course, and ending the experiment of the impact rockburst; and
    S5: under the action of the dynamic load in the step S3, if it is determined that no spalling phenomenon appears on the internal surface of the hole, unceasingly maintaining the state of loading the dynamic load in the step S3 by 2-10 minutes, to determine whether the spalling phenomenon appears in the rock sample specimen, and if it is determined that the spalling phenomenon appears on the internal surface of the hole of the rock sample specimen, repeating the step S4 and the following experimental steps, and if it is determined that no spalling phenomenon appears on the internal surface of the hole of the rock sample specimen, stopping the loading the dynamic load, and increasing the static stress(es) of the one direction, the two directions or the three directions loaded onto the rock sample specimen, then repeating the step S2 and the following experimental steps, and if the rock sample specimen goes into the failure course, determining and recording the failure course, and ending the experiment of the impact rockburst.

2. The method according to claim 1, wherein in the step S1, the rock sample specimen is obtained from a rock mass at a site to be excavated.

3. The method according to claim 1, wherein in the step S4 and S5, if the rock sample specimen is not damaged, after the loading the dynamic load is stopped, increasing the static stress(es) of the one direction, the two directions or the three directions loaded onto the rock sample specimen, wherein an increased amount of the static stress(es) of the one direction, the two directions or the three directions is(are) of the same intensity as that of the dynamic load loaded onto the rock sample specimen in the step S3.

4. The method according to claim 1, wherein in the step S2, a manner of loading the static stresses is a force loading manner or a strain loading manner, wherein, when the strain loading method is adopted, a loading rate is 0.004-0.2 mm/s, and when the force loading method is adopted, the loading rate is 0.05-2 kN/s.

5. The method according to claim 1, wherein in the step S1, a cross section of the through hole or the half hole in the rock sample specimen has a shape of circular, half circular, or horseshoe.

6. The method according to claim 1, wherein in the step S1, the rock sample specimen is made in a joint structure, and the rock sample specimen made in the joint structure is obtained by being collected from the site and then being further processed, or made by the following steps:
   (1) making up a plurality of plasterboards or resin plates, and drying the plurality of the plasterboards or the resin plates by air, wherein each of the plasterboards has a thickness of 5~10 mm, and each of the resin plates has a thickness of 3~8 mm;
   (2) bonding the plurality of the dried plasterboards or the dried resin plates together to form a laminate body by using an adhesive, and then drying the laminate body by air;
   (3) cutting the dried laminate body of the plasterboards into a required size according to a joint strike, and forming the hole at a position of a centre line of the laminate body, so as to obtain the rock sample specimen in the joint structure.

7. The method according to claim 1, wherein in the step S3, a disturbance signal of the dynamic load comprises: a cyclic wave disturbance signal, a single pulse disturbance signal, a step pulse disturbance signal, a noise wave disturbance signal, or a complex wave disturbance signal formed by superposing any of the above cyclic wave disturbance signal with a slope wave, or a superposed disturbance signal formed by superposing the complex wave disturbance signal with the noise wave disturbance signal.

8. The method according to claim 1, wherein the method further comprises a step of recording and/or a step of photographing, wherein, when the spalling phenomenon appears on the surface of the rock sample specimen, the failure course is recorded and/or photographed by using a micro camera.

9. An experimental method for simulating an impact rockburst, the method comprising;
   S1: making a rock sample specimen having a through hole or a half hole;
   S2: loading initial static stresses of three directions onto the rock sample specimen, and maintaining the initial static stresses of the three directions, to simulate a situation that an excavated tunnel suffers the static stresses;
   S3: loading dynamic load(s) of one direction, two directions or three directions onto the rock sample specimen by 0.5-10 minutes, so as to determine whether a spalling phenomenon appears on an internal surface of the through hole or the half hole, wherein the dynamic load is used to simulate the disturbance wave induced by an excavation, a blasting, an earthquake or a mechanical vibration;
   S4: under an action of the dynamic load in the step S3, if it is determined that the spalling phenomenon appears on the internal surface of the hole, unceasingly maintaining a state of loading the dynamic load in the step S3 by 0.5~10 minutes, to determine whether the rock sample specimen is further damaged, and if the rock sample specimen is not further damaged, stopping the loading the dynamic load, and increasing an intensity value of the dynamic load, then repeating the step S3 and the following experimental steps, and if the rock sample specimen goes into a failure course, determining and recording the failure course, and ending the experiment of the impact rockburst; and
   S5: under the action of the dynamic load in the step S3, if it is determined that no spalling phenomenon appears on the internal surface of the hole, unceasingly maintaining the state of loading the dynamic load in the step S3 by 2-10 minutes, to determine whether the spalling phenomenon appears in the rock sample specimen, and if it is determined that the spalling phenomenon appears on the internal surface of the hole of the rock sample specimen, repeating the step S4 and the following experimental steps, and if it is determined that no spalling phenomenon appears on the internal surface of the hole of the rock sample specimen, stopping the loading the dynamic load, and increasing the intensity value of the dynamic load, then repeating the step S3 and the following experimental steps, and if the rock sample specimen goes into the failure course, determining and recording the failure course, and ending the experiment of the impact rockburst.

10. The method according to claim 9, wherein in the step S1, the rock sample specimen is obtained from a rock mass at a site to be excavated.

11. The method according to claim 9, wherein in the step S4 and S5, if the rock sample specimen is not damaged, after the loading the dynamic load is stopped, increasing the static stress(es) of the one direction, the two directions or the three directions loaded onto the rock sample specimen, wherein an increased amount of the static stress(es) of the one direction, the two directions or the three directions is(are) of the same intensity as that of the dynamic load loaded onto the rock sample specimen in the step S3.

12. The method according to claim 9, wherein in the step S2, a manner of loading the static stresses is a force loading manner or a strain loading manner, wherein, when the strain loading method is adopted, a loading rate is 0.004-0.2 mm/s, and when the force loading method is adopted, the loading rate is 0.05-2 kN/s.

13. The method according to claim 9, wherein in the step S1, a cross section of the through hole or the half hole in the rock sample specimen has a shape of circular, half circular, or horseshoe.

14. The method according to claim 9, wherein in the step S1, the rock sample specimen is made in a joint structure, and the rock sample specimen made in the joint structure is obtained by being collected from the site and then being further processed, or made by the following steps:
   (1) making up a plurality of plasterboards or resin plates, and drying the plurality of the plasterboards or the resin plates by air, wherein each of the plasterboards has a thickness of 5~10 mm, and each of the resin plates has a thickness of 3~8 mm;
   (2) bonding the plurality of the dried plasterboards or the dried resin plates together to form a laminate body by using an adhesive, and then drying the laminate body by air;
   (3) cutting the dried laminate body of the plasterboards into a required size according to a joint strike, and forming the hole at a position of a centre line of the laminate body, so as to obtain the rock sample specimen in the joint structure.

15. The method according to claim 9, wherein in the step S3, a disturbance signal of the dynamic load comprises: a cyclic wave disturbance signal, a single pulse disturbance signal, a step pulse disturbance signal, a noise wave disturbance signal, or a complex wave disturbance signal formed by superposing any of the above cyclic wave disturbance signal with a slope wave, or a superposed disturbance signal formed by superposing the complex wave disturbance signal with the noise wave disturbance signal.

16. The method according to claim 11, wherein the method further comprises a step of recording and/or a step of photographing, wherein, when the spalling phenomenon appears on the surface of the rock sample specimen, the failure course is recorded and/or photographed by using a micro camera.

17. The method according to claim 2, wherein the method further comprises a step of recording and/or a step of photographing, wherein, when the spalling phenomenon appears on the surface of the rock sample specimen, the failure course is recorded and/or photographed by using a micro camera.

18. The method according to claim 3, wherein the method further comprises a step of recording and/or a step of photographing, wherein, when the spalling phenomenon appears on the surface of the rock sample specimen, the failure course is recorded and/or photographed by using a micro camera.

19. The method according to claim 12, wherein the method further comprises a step of recording and/or a step of photographing, wherein, when the spalling phenomenon appears on the surface of the rock sample specimen, the failure course is recorded and/or photographed by using a micro camera.

20. The method according to claim 13, wherein the method further comprises a step of recording and/or a step of photographing, wherein, when the spoiling phenomenon appears on the surface of the rock sample specimen, the failure course is recorded and/or photographed by using a micro camera.

* * * * *